(12) United States Patent
Beg et al.

(10) Patent No.: US 9,014,451 B2
(45) Date of Patent: Apr. 21, 2015

(54) SYSTEM AND METHOD FOR RAPID OCT IMAGE ACQUISITION USING COMPRESSIVE SAMPLING

(75) Inventors: Mirza Faisal Beg, Coquitlam (CA); Evgeniy Lebed, Coquitlam (CA); Marinko V. Sarunic, Coquitlam (CA)

(73) Assignee: Simon Fraser University, Burnaby (CA)

(*) Notice: Subject to any disclaimer, the term of this patent is extended or adjusted under 35 U.S.C. 154(b) by 264 days.

(21) Appl. No.: 13/819,713

(22) PCT Filed: Aug. 31, 2011

(86) PCT No.: PCT/CA2011/050532
§ 371 (c)(1),
(2), (4) Date: Feb. 27, 2013

(87) PCT Pub. No.: WO2012/027849
PCT Pub. Date: Mar. 8, 2012

(65) Prior Publication Data
US 2013/0156283 A1    Jun. 20, 2013

Related U.S. Application Data

(60) Provisional application No. 61/378,931, filed on Aug. 31, 2010.

(30) Foreign Application Priority Data

Apr. 21, 2011  (CA) ..................................... 2737822

(51) Int. Cl.
*G06K 9/00* (2006.01)
*G06T 11/00* (2006.01)
(Continued)

(52) U.S. Cl.
CPC ............. *G06T 11/005* (2013.01); *A61B 5/0066* (2013.01); *G01N 21/4795* (2013.01)

(58) Field of Classification Search
CPC ............. G01B 9/02091; A61B 5/0066; A61B 5/0073; A61B 3/102; G01N 21/4795; G01N 2021/1787; G06T 11/005
USPC .................................. 382/100, 128–132, 154
See application file for complete search history.

(56) References Cited

U.S. PATENT DOCUMENTS 7,145,661 B2   12/2006   Hitzenberger
7,532,772 B2   5/2009    Brady
(Continued)

FOREIGN PATENT DOCUMENTS

| CA | 2737822 | 2/2012 |
| WO | WO 2010/009447 | 1/2010 |
| WO | WO 2012/027849 | 3/2012 |

OTHER PUBLICATIONS

E.J. Candes and D. L. Donoho, New Tight Frames of Curvelets and Optimal Representations of Objects with Piecewise-C2 Singularities, Communications on Pure and Applied Mathematics, 57, No. 2,219-266 (2004).

(Continued)

*Primary Examiner* — Shefali Goradia
(74) *Attorney, Agent, or Firm* — Palmer IP

(57) ABSTRACT

A method for rapid OCT image acquisition includes acquiring by OCT a plurality of compressive measurements (y) representing a set of under-sampled OCT data in a Dirac domain below a Nyquist rate by sampling an object of interest at randomly spaced vertical and horizontal lines in a Cartesian geometry using a raster scan, and recovering a 3D volumetric OCT image (f) from the compressive measurements (y) using compressive sampling. The method may also include recovering the 3D volumetric OCT image (f) from the compressive measurements (y) based at least in part on a sparsifying matrix (S) capable of transforming the 3D volumetric OCT image (f) into a sparse representation, such as a matrix representation of the 3D volumetric OCT image (f) in a shift-invariant wavelet transform domain. The method may also be applied to radial OCT scan patterns.

21 Claims, 15 Drawing Sheets

(51) Int. Cl.
*A61B 5/00* (2006.01)
*G01N 21/47* (2006.01)

(56) References Cited

U.S. PATENT DOCUMENTS

| | | | |
|---|---|---|---|
| 7,646,924 B2 | 1/2010 | Donoho | |
| 8,446,593 B1* | 5/2013 | Ellerbee | 356/497 |
| 2008/0100612 A1 | 5/2008 | Dastmalchi et al. | |
| 2008/0140341 A1* | 6/2008 | Ralston et al. | 702/155 |
| 2009/0080739 A1 | 3/2009 | Rogers et al. | |
| 2009/0270738 A1* | 10/2009 | Izatt et al. | 600/476 |
| 2009/0279098 A1* | 11/2009 | Ohbayashi et al. | 356/478 |

OTHER PUBLICATIONS

E.J. Candes, J. Romberg, and T. Tao, Robust Uncertainty Principles: Exact Signal Reconstruction from Highly Incomplete Frequency Information, IEEE Trans. Inform. Theory, 52,489-509 (2004).

F. Herrmann and G. Hennenfent. Non-parametric seismic data recovery with curvelet frames. Geophysical Journal International, 173(1):233-248, (2008).

G. Hennenfent. Sampling and reconstruction of seismic wavefields in the curvelet domain. Graduate Thesis, University of British Columbia, (2008).

R. Baraniuk. Compressive sensing. IEEE Signal Processing Magazine, 24(4):118-121, (2007).

E. Candes, "Compressive Sampling", Proceedings of the International Congress of Mathematicians, Madrid, Spain (2006).

Boyd, S., Vandenberghe, L., Convex Optimization. Cambridge University Press, Cambridge (2004).

D. L. Donoho."Compressed sensing," Information Theory, IEEE Transactions on , vol. 52, No. 4, pp. 1289,1306, (2006).

N. Mohan, I. Stojanovic, W.C. Karl, B.E.A. Saleh, and M.G. Teich, "Compressed sensing in optical coherence tomography," in Three-Dimensional and Multidimensional Microscopy: Image Acquisition and Processing XVII, SPIE, 7570, 75700L (2010).

E. Lebed, "Sparse Signal Recovery in a Transform Domain", Graduate Thesis, The University of British Columbia, Vancouver, British Columbia (2008).

E. Lebed, P. J. Mackenzie, M. V. Sarunic, and M. F. Beg. Rapid volumetric OCT image acquisition using compressive sampling. Optics Express, 18(20): 21003-21012, (2010).

M. Young, E. Lebed, Y. Jian, P. J. Mackenzie, M. F. Beg, and M. V. Sarunic. Real-time high-speed volumetric imaging using compressive sampling optical coherence tomography. Biomedical Optics Express, 2(9):2690-2697, (2011).

E. Lebed, S. Lee, M. V. Sarunic and M. F. Beg. Rapid radial optical coherence tomography image acquisition. Journal of Biomedical Optics, 18(3):036004-13, (2013).

* cited by examiner

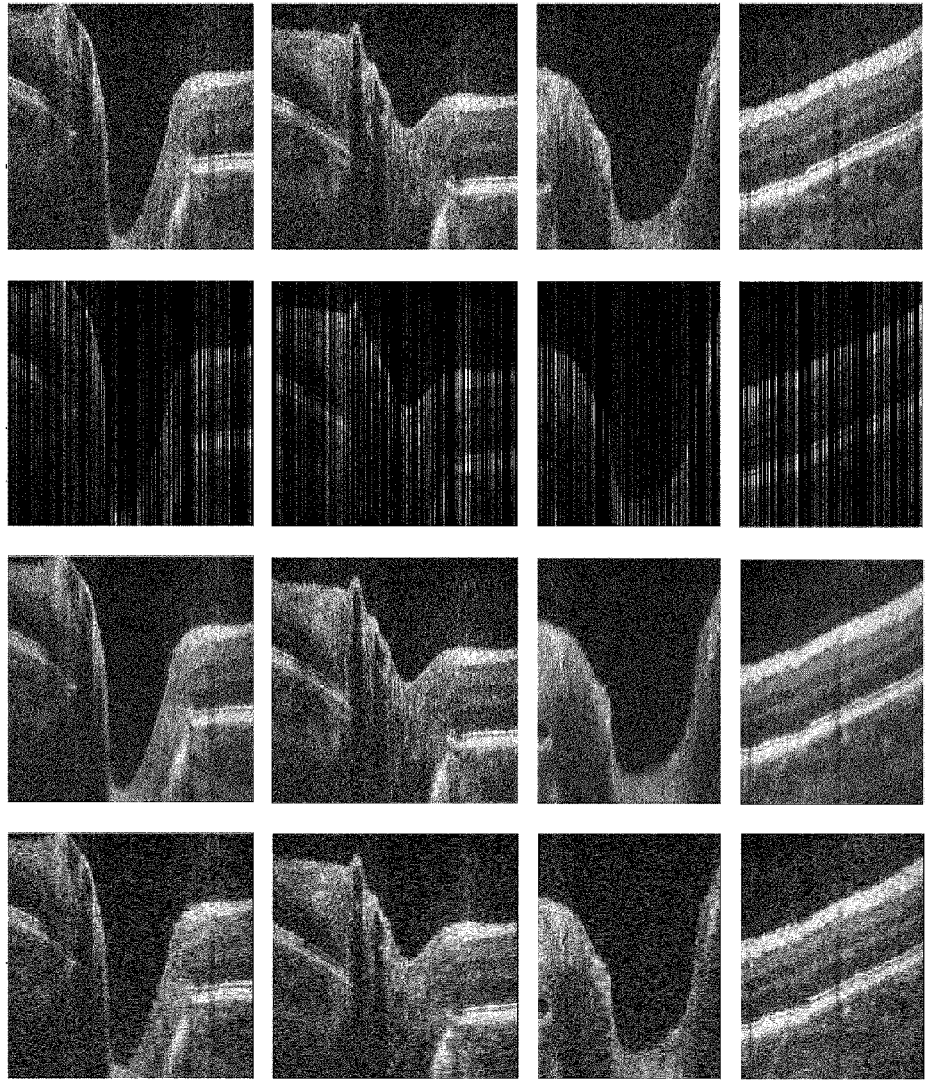
First row: FIG. 5A; 5B; 5C; 5D
Second row: FIG. 6A; 6B; 6C; 6D
Third row: FIG. 7A; 7B; 7C; 7D
Fourth row: FIG. 8A; 8B; 8C; 8D

SYSTEM AND METHOD FOR RAPID OCT IMAGE ACQUISITION USING COMPRESSIVE SAMPLING

1. TECHNICAL FIELD

The present invention relates generally to the field of signal acquisition and reconstruction, and more particularly, to the field of signal acquisition and reconstruction of images acquired using Optical Coherence Tomography ("OCT").

2. BACKGROUND OF THE INVENTION

Optical Coherence Tomography (hereinafter referred to as "OCT") is emerging as a dominant medical imaging modality for diagnostic ophthalmology. Optical coherence tomography works similarly to ultrasound tomography, however substituting use of light waves instead of sound waves to reconstruct images of tissue layers based on the reflection of light from tissue interfaces. By using the time-delay, and/or magnitude variance information contained in the light waves which have been reflected from different depths inside a tissue sample, an OCT system can reconstruct a depth-profile of the sample structure. Three-dimensional images can then be created by scanning the light beam laterally across the sample surface to create a 3D tomographic grid. Conventional OCT scanning schemes suffer from a number of drawbacks. Morphometric analysis and clinical applications typically demand high resolution OCT images, which necessitate dense sampling, leading to long scan times. During such long scan times, a person subject to the OCT scan is often required to remain still, sometimes for up to ten seconds, with a fixed gaze on a point without blinking—a challenging feat even for the most determined and those without eye health issues. Long scan times may inevitably increase the likelihood of image corruption from motion artifacts, such as image blurring and ghosting resulting from the subject's eye blinking during an OCT scan session. Although some OCT systems may implement motion tracking features in an attempt to reduce the potential effect of motion artifacts in OCT images, such motion tracking systems typically do not reduce OCT scan times, and may in fact increase scan durations. Additionally, some subjects with eye problems more likely to require OCT scans may be unable to fixate their gaze or eye focus for long OCT scan sessions which may be required by conventional OCT image acquisition. An outstanding need therefore exists for an improved system and method for OCT image acquisition for the benefits of reduced scan times, without significantly comprising the quality of the image acquired from the subject of interest.

Compressive sampling, or compressive sensing, is a technique for signal acquisition and reconstruction utilizing the prior knowledge that the sampled signal is sparse or compressible in nature. Conventional acquisition and reconstruction of images from frequency data using compressive sampling techniques typically follows the basic principle of the Nyquist density sampling theory, which states that to reconstruct an image, the number of Fourier samples that need to be acquired must match the desired resolution, and by extension, the number of pixels of the image. Compressive sampling suggests the possibility of new data acquisition protocols that show that super-resolved signals and images may be reconstructed from far fewer data or measurements than that which was considered necessary under the Nyquist sampling theory. An overview of compressive sampling may be found, for example, in E. J. Candes, J. Romberg, and T. Tao, *Robust Uncertainty Principles: Exact Signal Reconstruction from Highly Incomplete Frequency Information*, IEEE Trans. Inform. Theory, 52, 489-509 (2004); and E. J. Candes and D. L. Donoho, *New Tight Frames of Curvelets and Optimal Representations of Objects with Piecewise-C2 Singularities*, Communications on Pure and Applied Mathematics, 57, no. 2, 219-266 (2004).

3. SUMMARY OF THE INVENTION

Certain features, aspects and examples disclosed herein are directed to a method for rapid OCT image acquisition. Additional features, aspects and examples are discussed in more detail herein.

In accordance with a first embodiment of the invention, a method for rapid OCT image acquisition is provided. The exemplary method for rapid OCT image acquisition includes acquiring by OCT a plurality of compressive measurements (y) representing a set of under-sampled OCT data in a Dirac domain below a Nyquist rate by sampling an object of interest at randomly spaced vertical and horizontal lines in a Cartesian geometry using a raster scan, and recovering a 3D volumetric OCT image (f) from the compressive measurements (y) using compressive sampling.

Exemplary embodiments of the above-described method of the present invention may additionally include one or more of the following features. In some embodiments, a method for rapid OCT image acquisition further includes forming a sparsifying matrix (S) capable of transforming the 3D volumetric OCT image (f) into a sparse representation, and recovering the 3D volumetric OCT image (f) from the compressive measurements (y) based at least in part on the sparsifying matrix (S). According to certain embodiments, the sparsifying matrix (S) represents a matrix representation of the 3D volumetric OCT image (f) in a shift-invariant wavelet transform domain.

In some embodiments, the compressive measurements (y) represent a range between 25 and 77 percent of the data present in the 3D volumetric OCT image (f). In other embodiments, the compressive measurements (y) represent less than 50 percent of the data present in the 3D volumetric OCT image (f).

In accordance with a further embodiment of the present invention, another method for rapid Optical Coherence Tomography image acquisition is provided. In such exemplary embodiment, the method for rapid OCT image acquisition comprises acquiring by Optical Coherence Tomography a plurality of compressive measurements (y) representing a set of under-sampled Optical Coherence Tomography data in a Dirac domain below a Nyquist rate by sampling an object of interest at randomly angularly spaced radial scan lines in a radial geometry using a radial scan. The exemplary method further comprises mapping said compressive measurements (y) from said radial geometry to a Cartesian grid having radial coordinates; recovering a set of recovered radial scan images (f) from the compressive measurements (y) using compressive sampling; and mapping said recovered radial scan images from said Cartesian grid to a 3D Cartesian geometry having Cartesian coordinates to produce a physical 3D volumetric Optical Coherence Tomography image.

In some embodiments, the compressive measurements (y) represent a range between about 12 and 40 percent of the data present in the set of recovered radial scan images (f). In other embodiments, mapping said compressive measurements (y) from said radial geometry to a Cartesian grid having radial coordinates additionally comprises mapping the radial coordinate θ to the x Cartesian grid coordinate, and mapping the radial coordinate r to the y Cartesian grid coordinate. In yet further embodiments, mapping said recovered radial scan images from said Cartesian grid to a 3D Cartesian geometry having Cartesian coordinates additionally comprises using the transform θ=x and r=y.

In a particular embodiment of the present invention, the method for rapid Optical Coherence Tomography image acquisition may be adapted for use with either time-domain and/or Fourier domain OCT (also known as spectral domain OCT and/or swept source domain OCT) systems and imaging technologies, and also for use with other imaging systems, and in further alternative embodiments may be adapted for particular use with alternative emissive imaging means comprising one or more of: ultrasound, magnetic resonance and x-ray imaging.

Further advantages of the invention will become apparent when considering the drawings in conjunction with the detailed description.

4. BRIEF DESCRIPTION OF THE DRAWINGS

The present invention will now be described with reference to the accompanying drawing figures, in which:

FIGS. 5A-5D show two vertical and horizontal original B-scans acquired by conventional OCT raster-scan geometry.

FIGS. 6B-6D show the same slices as FIGS. 5A-5D taken from a volume with 53% missing data according to an embodiment of the invention.

FIGS. 7A-7D show the same slices as FIGS. 5A-5D recovered from the compressive measurements by the CS interpolation method according to an embodiment of the invention.

FIGS. 8A-8D show the same slices as FIGS. 5A-5D recovered by a conventional bilinear interpolation of the same B-scans.

Figure 13:
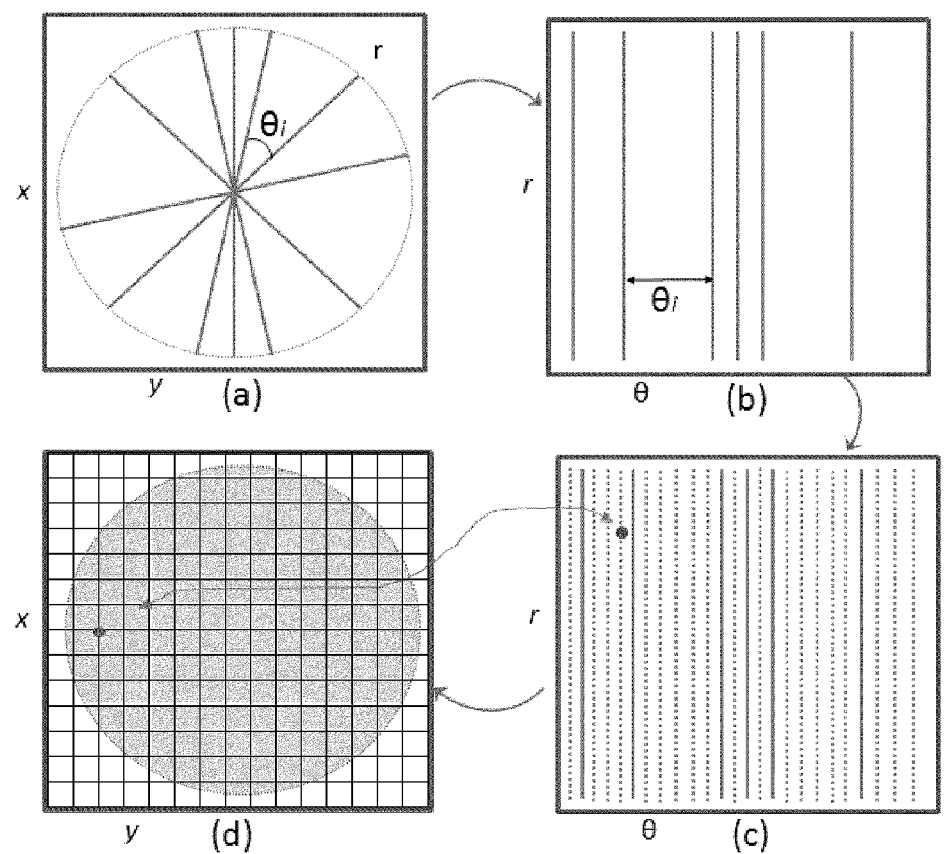

FIG. 13 illustrates a schematic representation of a radial OCT scanning pattern shown in FIG. 13(a); a schematic representation of radial OCT scan data mapped to a Cartesian transform grid shown in FIG. 13(b); a schematic representation of interpolation and reconstruction of radial OCT scan data using compressive sampling shown in FIG. 13(c); and a schematic representation of interpolated radial OCT scan data mapped to a Cartesian physical grid for analysis and display shown in FIG. 13(d), all according to an embodiment of the invention.

Figure 14A:
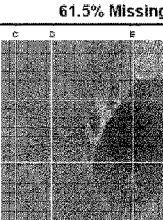
Figure 14D:
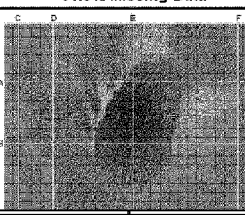

FIG. 14 illustrates in its top row, a typical en-face slice image extracted from a full OCT data volume of an optic nerve head acquired using a conventional OCT raster scan geometry, showing the en-face slice represented in three frames overlaid with random radial subsampling masks corresponding to 200 radial scans (61.5% missing data compared to conventional raster scan) in the left frame, 100 radial scans (80.9% missing data) in the center frame, and 60 radial scans (88.3% missing data) in the right frame, according to an embodiment of the invention. The yellow lines on the overlaid en-face slice images show locations of six exemplary extracted B-scans further shown in FIG. 14A to FIG. 14F.

FIG. 14A illustrates in a series of frames from left to right, the exemplary B-scan labeled "A" extracted from a full conventionally raster-acquired OCT volume shown in the top row of FIG. 14; the same exemplary extracted B-scan corresponding to a random radial subsampling mask which discards 61.5% of the raster data (corresponding to 200 radial scans); a corresponding exemplary reconstructed B-Scan recovered from the remaining subsampled data in the 200 radial scan volume using compressive sampling; the exemplary B-scan corresponding to a random radial subsampling mask which discards 80.9% of the raster data (corresponding to 100 radial scans); a corresponding exemplary reconstructed B-Scan recovered from the remaining subsampled data in the 100 radial scan volume using compressive sampling; the exemplary B-scan corresponding to a random radial subsampling mask which discards 88.3% of the raster data (corresponding to 60 radial scans); and a corresponding exemplary reconstructed B-Scan recovered from the remaining subsampled data in the 60 radial scan volume using compressive sampling, according to an embodiment of the invention.

FIG. 14B illustrates in a series of frames from left to right, the exemplary B-scan labeled "B" extracted from a full conventionally raster-acquired OCT volume shown in the top row of FIG. 14; the same exemplary extracted B-scan corresponding to a random radial subsampling mask which discards 61.5% of the raster data (corresponding to 200 radial scans); a corresponding exemplary reconstructed B-Scan recovered from the remaining subsampled data in the 200 radial scan volume using compressive sampling; the exemplary B-scan corresponding to a random radial subsampling mask which discards 80.9% of the raster data (corresponding to 100 radial scans); a corresponding exemplary reconstructed B-Scan recovered from the remaining subsampled data in the 100 radial scan volume using compressive sampling; the exemplary B-scan corresponding to a random radial subsampling mask which discards 88.3% of the raster data (corresponding to 60 radial scans); and a corresponding exemplary reconstructed B-Scan recovered from the remaining subsampled data in the 60 radial scan volume using compressive sampling, according to an embodiment of the invention.

FIG. 14C illustrates in a series of frames from left to right, the exemplary B-scan labeled "C" extracted from a full conventionally raster-acquired OCT volume shown in the top row of FIG. 14 and the corresponding subsampled and recovered B-scan images corresponding to 200, 100 and 60 radial scan volumes, similar to as described above in FIGS. 14A and 14B, according to an embodiment of the invention.

FIG. 14D illustrates in a series of frames from left to right, the exemplary B-scan labeled "D" extracted from a full conventionally raster-acquired OCT volume shown in the top row of FIG. 14 and the corresponding subsampled and recovered B-scan images corresponding to 200, 100 and 60 radial scan volumes, similar to as described above in FIGS. 14A and 14B, according to an embodiment of the invention.

FIG. 14E illustrates in a series of frames from left to right, the exemplary B-scan labeled "E" extracted from a full conventionally raster-acquired OCT volume shown in the top row of FIG. 14 and the corresponding subsampled and recovered B-scan images corresponding to 200, 100 and 60 radial scan volumes, similar to as described above in FIGS. 14A and 14B, according to an embodiment of the invention.

FIG. 14F illustrates in a series of frames from left to right, the exemplary B-scan labeled "F" extracted from a full conventionally raster-acquired OCT volume shown in the top row of FIG. 14 and the corresponding subsampled and recovered B-scan images corresponding to 200, 100 and 60 radial scan volumes, similar to as described above in FIGS. 14A and 14B, according to an embodiment of the invention.

Figure 15A:
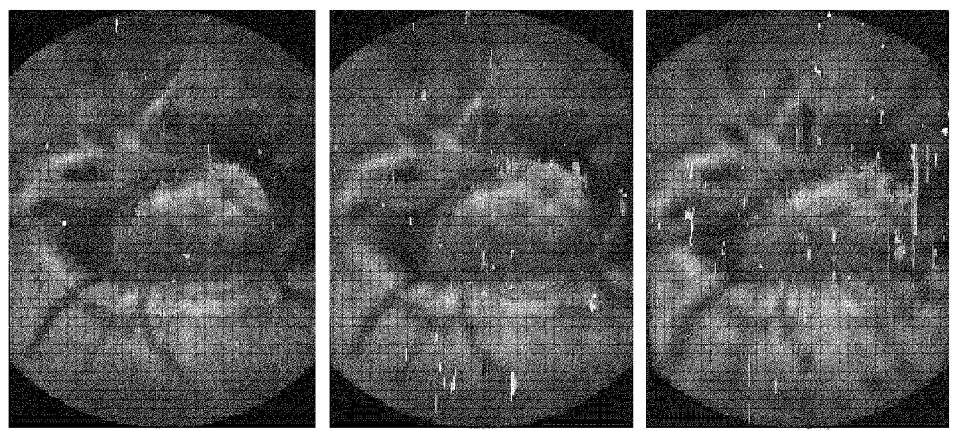

FIG. 15A illustrates a Topographical Change Analysis (TCA) map showing the position of an ILM surface relative to the mean overlaid on top of summed-voxels-projection images of a recovered OCT volume at 61.5% missing data corresponding to a 200 radial B-scan volume, according to an embodiment of the invention.

FIG. 15B illustrates a TCA map showing the position of an ILM surface relative to the mean overlaid on top of summed-voxels-projection images of a recovered OCT volume at 80.9% missing data corresponding to a 100 radial B-scan volume, according to an embodiment of the invention.

FIG. 15C illustrates a TCA map showing the position of an ILM surface relative to the mean overlaid on top of summed-voxels-projection images of a recovered OCT volume at 88.3% missing data corresponding to a 60 radial B-scan volume, according to an embodiment of the invention.

Similar reference numerals refer to corresponding parts throughout the several views of the drawings.

5. DETAILED DESCRIPTION OF THE INVENTION

To address certain shortcomings of the aforementioned prior art OCT scanning methods, in one embodiment the present invention provides a method for rapid OCT image acquisition using compressive sampling, in which OCT acquisition of a reduced random or pseudo-random subset of the raster scans that make up the 3D volumetric field of view of the entire image of a subject of interest is performed during the scanning process. Thereafter, by exploiting the sparsity of image coefficients in a predetermined transform domain (e.g. a shift-invariant wavelet transform domain), the recovery of missing samples may desirably be achieved with high fidelity, thereby reducing the overall OCT scan time and the associated patient discomfort and motion artifacts that may typically follow slower conventional OCT scanning schemes, while recovering a full 3D image of the scanned volume. The systems and methods disclosed in the present specification may be applied to both Fourier domain (also known as spectral domain and/or swept source) and time-domain based OCT image acquisition methodologies and applications according to embodiments of the present invention. In further alternative embodiments of the present invention, the systems and methods disclosed in the present specification may also be adapted for use with other imaging systems, and in particular alternative embodiments may be adapted for use with alternative emissive imaging means comprising one or more of: ultrasound, magnetic resonance and x-ray imaging, for example.

Compressive Sampling

To clarify the advantages and benefits of the present method for rapid OCT image acquisition using compressive sampling as disclosed according to embodiments of the invention herein, a discussion of compressive sampling is provided.

Prior to the introduction of compressive sampling, conventional wisdom as exemplified by the Nyquist sampling theorem states that a signal needs to be sampled at a rate greater than the inverse of twice its bandwidth to permit perfect signal reconstruction, commonly referred to as the Nyquist sampling rate. If the signal is a vector of length N, then the acquisition of at least N number of samples is required to reconstruct that signal according to Nyquist sampling methods. The sensing or measurement matrix is therefore a N*N square matrix.

Compressive sampling however permits accurate signal reconstruction from highly under-sampled measurements, i.e. data sampled at significantly below the Nyquist rate. In particular, it has been shown that when the unknown signal has an S-sparse representation, i.e. one can find a basis in which its representation has less than S non-zero entries, compressive sampling may desirably offer successful recovery with relatively few under-sampled measurements K, where K<<N. Accordingly, a sample measurement matrix may therefore be reduced to a K*N matrix. To allow for successful signal reconstruction, the theory of compressive sampling provides that the measurement matrix needs to be incoherent or uncorrelated with the sparsifying matrix used to transform the signal into its sparse representation, or satisfies the so-called Restricted Isometry Property (RIP). To satisfy the mutual incoherency criterion, random measurement matrices are often used since they will most likely be uncorrelated with any specific sparsifying matrix. See E. J. Candes, J. Romberg, and T. Tao, *Robust uncertainty principles: Exact recovery from highly incomplete Fourier information*, IEEE Trans. Inform. Theory, 52 489-509 (2004). Then, relying on the fact that the underlying signal is compressible, an appropriate non-linear method enforcing signal sparsity and consistency of the reconstruction with the acquired samples can be used to reconstruct the signal from randomly under-sampled data.

Accordingly, a successful application of compressive sampling can be said to have three requirements: 1) Transform sparsity—the desired image should have a sparse representation in a known transform domain (i.e. it must be compressible by transform coding); 2) Incoherence of under-sampling artifacts—the artifacts in linear reconstruction caused by K-spare under-sampling should be incoherent in the sparsifying domain; and 3) Nonlinear reconstruction—the image should be reconstructed by a non-linear method which simultaneously enforces sparsity of the image representation and consistency of the reconstruction with the acquired samples.

Transform Sparsity

As suggested by the theory of compressive sampling, successful signal recovery from under-sampled data depends in part on the signal having a sparse representation in a known transform domain. Hereinafter, a transform that provides sparse representation of 3D OCT image data in a basis different from one in which the image data is acquired is referred to as a "sparsifying transform", a mathematical operator that maps a vector of image data to a sparse vector. In a preferred embodiment of the invention, a suitable sparsifying transform for the method for rapid OCT image acquisition using compressive sampling to recover data may be chosen depending on several factors:

1. Sparsity. The sparsifying transform may desirably be able to capture most of the energy of the sampled OCT signal with only a few coefficients.
2. Incoherence. The basis functions of the sparsifying transform may desirably be as incoherent as possible with respect to the domain from which compressive signal measurements are acquired.
3. Tight frame. The sparsifying transform may desirably form a tight frame, or obey a generalized Parseval's identity.
4. The sparsifying transform may desirably pass the dot-test.

Suitable sparsifying transforms satisfying the above-mentioned four factors according to an embodiment of the invention may include the curvlet transform, surfacelet transform, and wavelet transform, for example. In a preferred embodiment of the method for rapid OCT image acquisition using compressive sampling, the sparsifying transform may be a shift-invariant wavelet transform.

In one embodiment of the method for rapid OCT image acquisition using compressive sampling, the problem of single recovery of a 3D volumetric OCT image from a subset of under-sampled OCT data may be characterized by the following forward model:

$$y = RMf + n \quad (1.1)$$

In the equation (1.1), f is a vector of N entries that denotes the 3D image of a subject of interest, such as a biological tissue structure for example, defined on a 3D Cartesian grid, obtainable by OCT using conventional raster scan geometry. In one embodiment of the invention, the method for rapid OCT image acquisition using compressive sampling proposes to recover the full 3D image f by taking K measurements of the full 3D image f at a sampling rate significantly below the Nyquist rate. The reduced number of measurements from which the full data vector f may be recovered are hereinafter referred to as compressive measurements or samples, represented by vector y in the equation (1.1) with K entries, where K<<N, and where each component of y is a linear measurement of the full data vector f. Symbol n represents the noise present in the acquired OCT data. In one embodiment of the present invention, the K compressive measurements represented by y may comprise a subset of measurements containing between 25% and 77% of the number of measurements or samples in the full 3D image f, for example.

The matrix M in equation (1.1) refers to the domain from which the compressive measurements y are acquired. In a preferred embodiment of the invention, the OCT is a Fourier domain or time-domain OCT, and OCT images are acquired in a 3D space with Cartesian geometry. As such, in the signal recovery problem as represented by the equation (1.1), M is the identity or the Dirac measurement basis such that $M:=I_d$, where identity matrix $I_d$ has a dimension of d×d. The matrix R is a restriction operator, i.e., it extracts those rows from the identity matrix M that represent the number of compressive measurements that are actually acquired. The dimensions of the measurement basis and the restriction operator may be determined by the acquisition geometry, or the raster scanning geometry of the OCT image acquisition system or scanning path.

As suggested by the theory of compressive sampling, the basis functions of the sparsifying transform selected in embodiments of the invention may desirably be as incoherent as possible with respect to the domain from which compressive measurements are acquired, and thereby represent mutual incoherency. It has been shown that sampling an object of interest in a measurement basis at randomly spaced vertical and horizontal lines in a Cartesian geometry skipping a large portion of the image during acquisition satisfies this mutual incoherency criterion, as random measurement matrices are often used since they will most likely be uncorrelated with any specific sparsifying matrix. See E. J. Candes, J. Romberg, and T. Tao, *Robust uncertainty principles: Exact recovery from highly incomplete Fourier information*, IEEE Trans. Inform. Theory, 52 489-509 (2004). In one embodiment of the present invention, the acquired subset of OCT image data or measurements, y, may be acquired corresponding to random vertical and horizontal lines imposed on the physical volume to be imaged. Such random vertical and horizontal scanning or measurement lines may be generated by a binary restriction mask R comprising vertical and horizontal lines with uniform and random placement, which may be applied during data acquisition such that certain random horizontal and vertical raster-scan lines are skipped during the raster-scanning process, thereby generating randomly sub-sampled OCT image volumes y of the 3D image of a subject of interest f. As such, the application of a restriction mask R results in the reduction in the number of samples being acquired as compared to a conventional OCT raster scan, as best illustrated by FIGS. 1 and 2.

Figure 1:
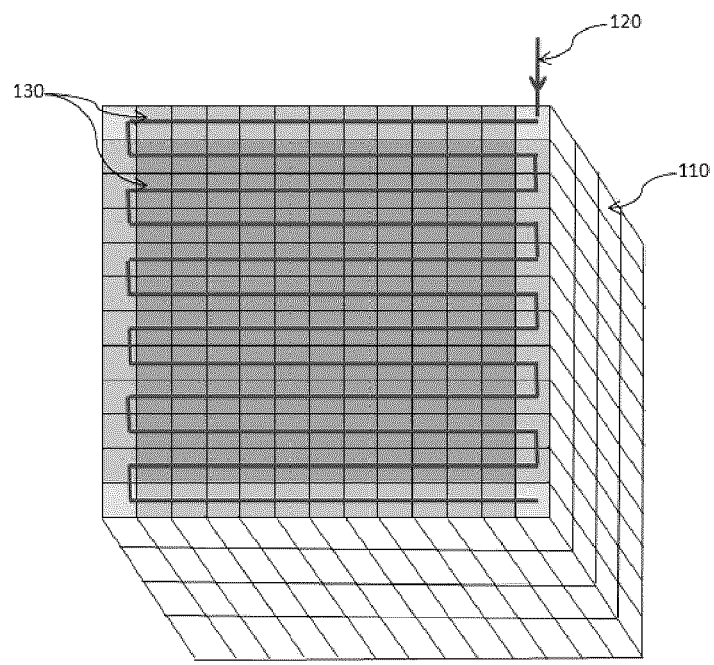
FIG. 1 illustrates a schematic view of a conventional OCT scan pattern.
Figure 2:
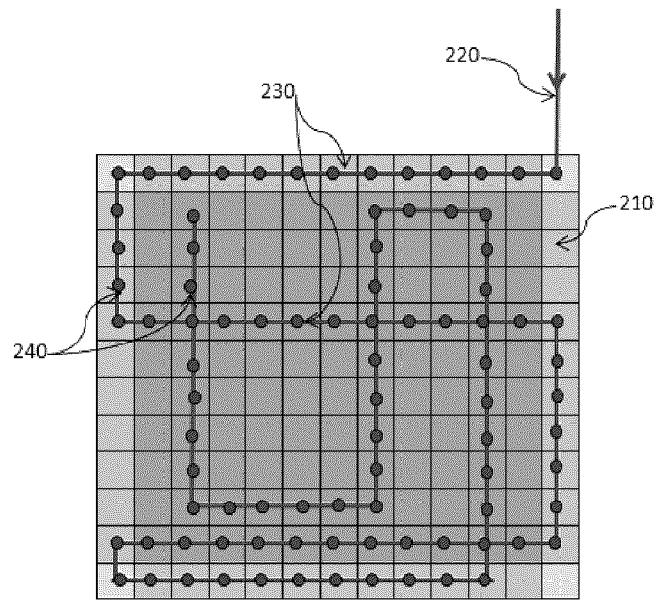
FIG. 2 illustrates a schematic view of an OCT scan pattern according to an embodiment of the present method for rapid OCT image acquisition using compressive sampling.

As shown in FIG. 1, which illustrates a schematic of a conventional OCT scan pattern, the volume of a subject of interest 110, which may comprise a biological body or tissue structure such as an human eye, is imaged by OCT using a typical raster scan geometry whereby every point in the volume is imaged by scanning every horizontal line 130 in the volume with a light beam 120. Put simply, 100% of the volume of the subject of interest 110 is scanned or imaged. In an embodiment of the present method for rapid OCT image acquisition using compressive sampling only random, fixed lines in the image volume are scanned or imaged to form compressively sampled OCT image data y. FIG. 2 illustrates a schematic of an OCT scan pattern according to an embodiment of the present method for rapid OCT image acquisition using compressive sampling. As shown in FIG. 2, a volume of a subject of interest 210 is imaged by scanning only selected, randomly-spaced fixed horizontal lines 230 and vertical lines 240, whereby only a subset of the raster scans that make up the 3D volumetric field of view of the entire image of a subject of interest is sampled. In one embodiment, compressive measurements represent 25% of the total raster scans that make up the 3D volumetric field of view of the entire image with 75% of the data missing. In other embodiments, compressive measurements represent subsets of 77%, 65%, 47% and 39% of the total raster scans of the entire image sampled, with 23%, 35%, 53%, and 61% of the data missing, respectively. Still in some embodiments, the compressive measurements (y) represent a range between 25 and 77 percent of the data present in the 3D volumetric OCT image (f). In other embodiments, the compressive measurements (y) represent less than 50 percent of the data present in the 3D volumetric OCT image (f).

Referring again to the signal recovery problem in equation (1.1), ignoring temporarily the noise n, a solution to the signal recovery problem is to solve a matrix equation of the form y=RMf. Since vector y is of length K and vector f is of length N with K<<N, this system of linear equations is underdetermined and does not have a unique solution in general. However, the theory of compressive sampling states that adding the constraint that the signal f is compressible enables one to solve this underdetermined system of linear equations. That is, if one can find a sparsifying transform domain represented by matrix S that offers good compressibility, i.e. a small number of coefficients x=Sf can describe the 3D image f in the sparsifying domain, then the signal f can be represented as f=$S^H$x, where $S^H$, the conjugate transpose of matrix S, is the synthesis operator transforming the coefficients x from the sparsifying domain back to the image domain represented by matrix M, or the domain from which compressive measurements are acquired and in which the signal is wished to be reconstructed. Therefore, given incomplete measurements y of the image f, instead of recovering the unknown image f directly, in an embodiment of the present invention, the unknown sparse coefficients x parameterizing f may be selected such that the reconstructed signal $S^H$x followed by the application of a known restriction mask R is close to the observed under-sampled data y, subject to the constraint that the $l_2$ mean-squared error $\|y-RS^Hx\|_2$ is small. Put in other words, given a set of incomplete measurements y of the signal f, an approximation ~f such is desired to be obtained such that (i) f~=$S^H$x~, where x~ is sparse, and (ii) $\|y-RS^Hx\|_2$ is small. From the many potential solutions to this problem, the desired x~ is one with the smallest $l_1$ norm $\|x^-\|_1$, representing a measure of sparsity. Therefore, the recovery of sparsely sampled OCT images may be realized by solving the following optimization problem via $l_1$ minimization:

$$x^- = \arg\min \|x^-\|_1 \text{ subject to } \|y-RS^Hx\|_2 \le \epsilon \quad (1.2)$$

In a preferred embodiment of the present invention, the matrix $S^H$ may be determined as a synthesis matrix in the shift-invariant wavelet domain which offers good compressibility of OCT images. Other sparsifying domains that offer good compressibility of OCT images and satisfy the conditions as discussed in the above-section titled "Transform Sparsity" may also be used in other embodiments of the invention.

The optimization problem in equation (1.2) is a convex optimization problem and may be cast into a linear program to solve the problem in equation (1.2), from which suitable conventional linear programs from the field of convex optimization may be employed. In a preferred embodiment of the present invention, the method for rapid OCT image acquisition using compressive sampling may employ the iterative soft thresholding (IST) solver to solve the $l_1$ minimization problem given in equation (1.2). Before the IST solver may be applied directly to solve the $l_1$ minimization problem, equation (1.2) is reformulated into a series of unconstrained problems using Lagrange multipliers λ as:

$$x^- = \arg\min \|x^-\|_1 + \lambda \|y-RS^Hx\|^2 \quad (1.3)$$

where λ is a parameter that controls the tradeoff between the sparsity of the solution (minimization of $l_1$ norm) and the $l_2$ data misfit. To simplify notation, a matrix A is defined to be A: $RMS^H$.

An exemplary IST program code according to an embodiment of the invention for solving the $l_1$ minimization problem may be represented as follows:

| | Result: Estimate for x |
|---|---|
| 1 | initialization; |
| 2 | $x_0$ ← initial guess for x; |
| 3 | $\lambda_0$ ← initial Lagrange multiplier; |
| 4 | L ← number of inner iterations; |
| 5 | while $\|y - Ax\|_2 \ge \epsilon$ do |
| 6 |    for l = 1 to L do |
| 7 |       i ← i + 1; |
| 8 |       $x_{i+1}$ ← $S_{\lambda k}$(xi + $A^H$ (y-$Ax_i$)); |
| 9 |    end |
| 10 |    $\lambda_{k+1}$ ← $\alpha_k \lambda_k$ with $0 < \alpha_k < 1$; |
| 11 |    k ← k + 1; |
| 12 | end |

Using the IST solver such as the above-described exemplary IST solution method, the iterative update x→$T_\lambda$(x+$A^T$(y−Ay)) desirably converges to the solution for a particular value of λ as the number of iterations goes to infinity. In practice, only a finite number of iterations may be required to achieve convergence of x~. According to an embodiment of the invention, after obtaining an approximation of the sparsifying coefficients $x^\lambda$, the full OCT image f is recovered by the following equation:

$$f^- = S^H x^- \quad (1.4)$$

In a preferred embodiment, the full 3D OCT image volume may be recovered with the IST solver using approximately six (6) inner loops and forty (40) outer loop iterations, for example.

In certain embodiments of the present inventive method for rapid OCT image acquisition using compressive sampling as above described thus far, the OCT system is a Fourier domain or time-domain OCT system and the measurement basis in which the compressive measurements are acquired may be the Dirac basis, however in other embodiments of the invention, other measurement bases may be utilized by way of modifying the OCT system hardware by which the OCT data is acquired, as may be obvious to a person skilled in the OCT art. In other embodiments, other measurement bases may be used, such as sparcifying transform matrices which form a tight-frame and pass a dot-test, for example. One way of checking whether a specific measurement matrix will allow for sparse solutions to be recovered and thereby be potentially suitable for utilization according to an embodiment of the present invention, is to check if the measurement matrix follows the Restricted Isometry Property (RIP).

Figure 3:
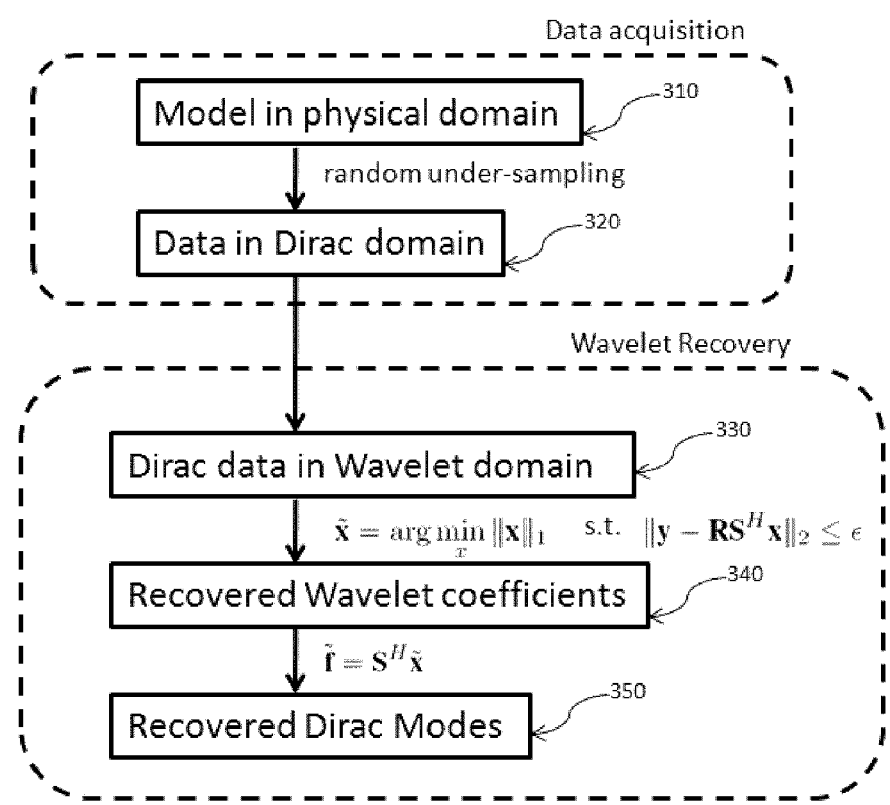
FIG. 3 illustrates a flow diagram of a method for rapid OCT image acquisition using compressive sampling according to an exemplary embodiment of the invention.

In a preferred embodiment of the invention, the IST solver is selected as the l1 minimization algorithm for its fast convergence and ease of implementation. However, in other embodiments, any other suitable known l1 minimization algorithms may be applied, such as iteratively reweighted least squares, SPGL1 solver, projected gradient methods, and iterative hard-thresholding, for example FIG. 3 illustrates a flow diagram of a method for rapid OCT image acquisition using compressive sampling according to exemplary embodiment of the invention. As shown at operation 310, the method begins with the modeling of the signal recovery problem as shown in equation (1.1) in the physical domain, or Fourier domain or time-domain OCT.

Following the modeling of the signal recovery problem, at step 320, K compressive measurements (y) representing a subset of the raster scans that make up the 3D volumetric field of view of the entire image (f) of a subject of interest are sampled in the Dirac domain by random under-sampling.

Following data acquisition at operations 310 and 320, the method for rapid OCT image acquisition using compressive sampling proceeds to signal reconstruction. At operation 330, a sparsifying domain that offers good compressibility of the full 3D image f is selected. In the embodiment as shown in FIG. 3, the sparsifying transform used is the shift-invariant wavelet transform. Next, the recovery of sparsely sampled OCT images modeled by the problem in equation (1.1) may be realized by solving the optimization problem via $l_1$ minimization in equation (1.2) using a suitable l1 minimization algorithm, such as using the IST solver to find an approximation of the sparsifying coefficients $\tilde{x}$ at step 340. Finally, the full 3D image $\tilde{f}$ is reconstructed using equation (1.4) in the physical domain, or Dirac basis at step 350.

Accordingly, as described by illustrative embodiments, the method for rapid OCT image acquisition using compressive sampling of the invention, by acquiring a small random or pseudo-random subset of the raster scans that make up the 3D volumetric field of view of the entire OCT image of a subject of interest, followed by exploiting the sparsity of image coefficients in a predetermined transform domain (e.g. shift-invariant wavelet transform domain), enables the recovery of missing samples with high fidelity, thereby advantageously reducing the overall OCT scan time and the associated patient discomfort and motion artifacts that typically follow conventional OCT scanning schemes.

EXAMPLES

Figure 4A:
FIG. 4A illustrates an exemplary transversal slice, or C-scan, extracted from a full OCT volume of an optic nerve head acquired using conventional OCT raster scan geometry.
Figure 4B:
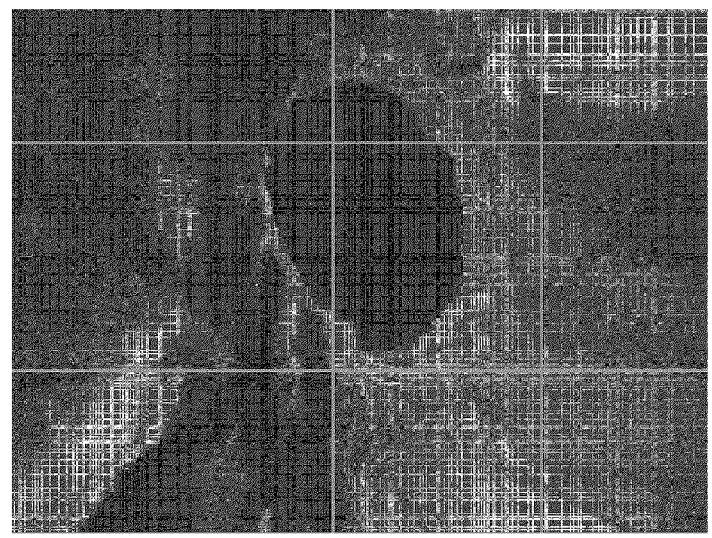
FIG. 4B illustrates a C-scan of a mask that discards 53% of the original samples as shown in FIG. 4A according to an embodiment of the invention.

A full 3D OCT original image volume (f) was acquired by raster-scanning the optic nerve head of a healthy male subject using OCT. An example of a transversal slice, or C-scan, extracted from the OCT volume is shown in FIG. 4A. To simulate the sparsely sampled OCT image volume (y) that would be acquired by a method of randomly skipping horizontal and vertical raster-scan lines to rapidly sub-sample the desired volume, a binary restriction mask R is applied to this full OCT image f. This mask R consists of vertical and horizontal lines with random (but fixed) placing. Five levels of restriction mask removing 23, 35, 53, 61, and 75 percent of sampled OCT data and corresponding to sub-sampling rates of 77, 65, 47, 39 and 25 percent, respectively, were created, and were applied to the original image volume to generate five different sub-sampled volumes y. An example of mask R that discards 53% of the original samples to represent a 47% sub-sampling rate is shown in FIG. 4B where the red lines denote data that was discarded. The four green lines represent recovered B-scans shown in FIGS. 5A-5D.

Figure 4C:
FIG. 4C illustrates C-scan of a reconstructed OCT volume recovered from 47% of the original samples as shown in FIG. 4A missing according to an embodiment of the invention.
Figure 4D:
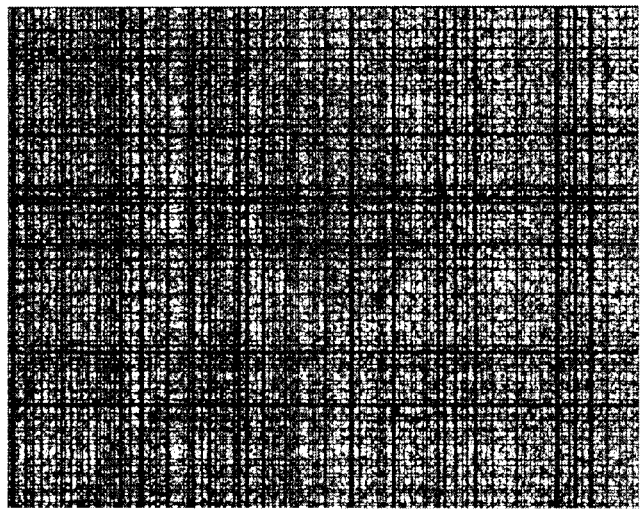
FIG. 4D shows contrast-enhanced differences between the results of FIG. 4A and FIG. 4C.

The full 3D OCT image volume for each level of subsampling was recovered according to an embodiment of the present method for rapid OCT image acquisition using compressive sampling employing an exemplary IST solver (detail: using 6 inner and 40 outer loop iterations). SNR based on recovered images corresponding to 23, 35, 53, 61, and 75 percent missing data was found to be 14.9, 13.0, 10.6, 9.8, and 7.5 db respectively showing decreasing SNR with increasing degradation due to missing data. The compressive sampling ('CS') recovery result for 53% missing data (corresponding to a 47% sub-sampling rate) and the error |f−$\tilde{f}$| image for this cross-section is shown in FIGS. 4C and 4D, respectively.

FIGS. 5A-5D show two vertical (FIGS. 5A and 5B) and horizontal (FIGS. 5C and 5D) original B-scans acquired from conventional OCT using raster-scan geometry. FIGS. 6A-6D show the same slices as FIGS. 5A-5D, respectively, taken from an image volume with 53% missing data, corresponding to an imaging sampling rate of 47% of the total volume desired to be imaged. FIGS. 7A-7D show the same slices as FIGS. 5A-5D, respectively, after recovery from the compressed or sparsely sampled scan slices shown in FIGS. 6A-6D using the CS interpolation method as detailed above according to an embodiment of the invention. FIGS. 8A-8D show the same slices as FIGS. 5A-5D, respectively, recovered by bilinear interpolation of the same B-scans of FIGS. 5A-5D.

Comparing the two vertical and horizontal B-scans recovered from a volume with 53% missing data (corresponding to a compressive sampling rate of 47%) using the CS interpolation method as are shown in FIGS. 7A-7D with bilinear interpolation of the same B-scans as shown in FIGS. 8A-8D, one can observe a distinct, undesirable "staircase" pattern or artifact in the bilinear interpolation results which are desirably absent in the CS-based image recovery.

Figure 9A:
FIGS. 9A-9D show representative typical B-scans recovered according to an embodiment of the invention utilizing compressive sampling in volumes with 23, 35, 61 and 75 percent missing data.
Figure 9B:
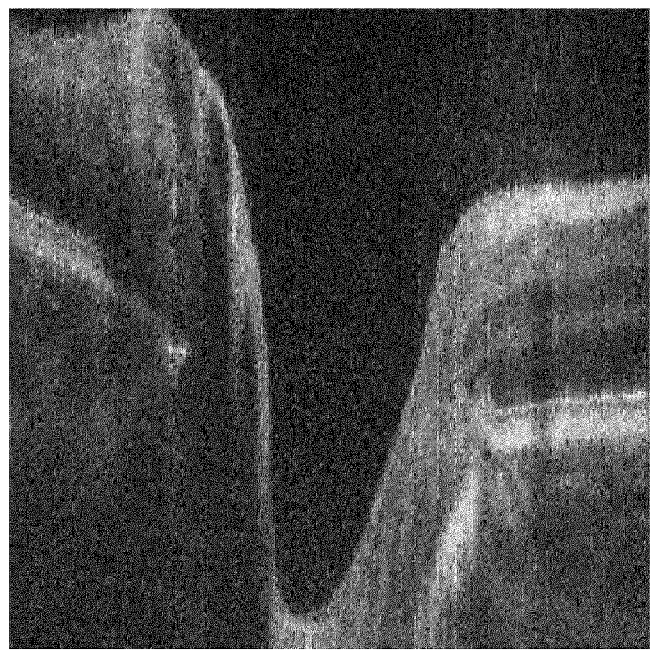
Figure 9C:
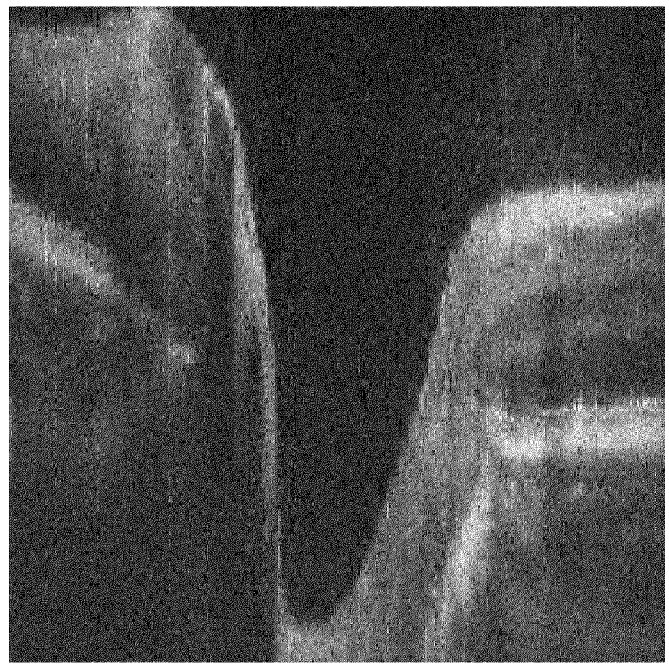
Figure 9D:
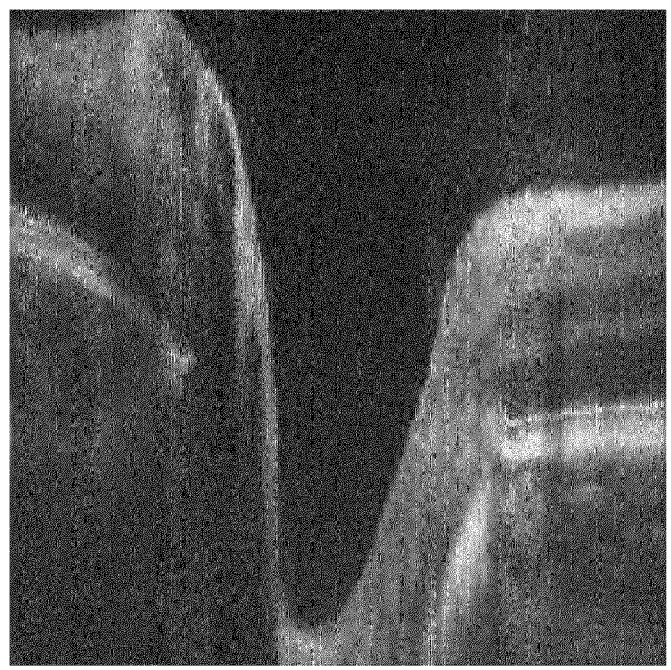

FIGS. 9A-9D show representative typical B-scans recovered using the CS interpolation in imaged volumes with 23, 35, 61 and 75 percent missing data, respectively (corresponding to compressive sampling rates of 77, 65, 29 and 25 percent, respectively), from a region where data was not sampled. It can be seen that the overall image quality begins to deteriorate progressively from FIGS. 9A to 9D as more data is discarded (corresponding to less data acquired in a compressed sampling acquisition scan), but nevertheless, the fidelity is still acceptable even for an image volume recovered from a scan with 25% sampling (or 75% missing data as compared to a full scan) as shown in FIG. 9D.

Validation

Experiments were performed to quantify how the degradation in recovered images affected the measurement of anatomically meaningful parameters such as the optic nerve cup shape from ophthalmologic OCT image volumes acquired using compressive sampling scanning and recovery methods such as disclosed above according to embodiments of the present invention. This was done by manually segmenting, using established protocols, the clinically relevant Inner Limiting Membrane ("ILM") surface for the reconstructed image volume for each of five exemplary levels of image degradation. These segmentations were performed on each B-scan slice of every volume.

Figure 10A:
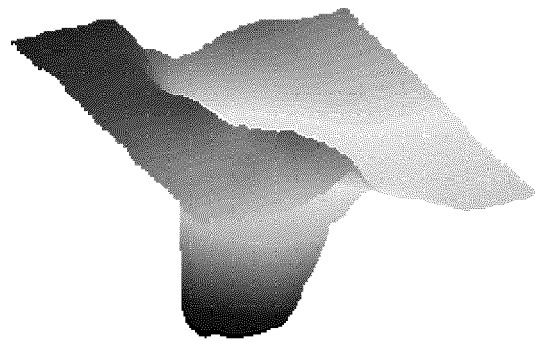
FIG. 10A shows an extracted ILM surface from a segmentation of the original 3D image volume acquired using a conventional OCT raster scan geometry.
Figure 10B:
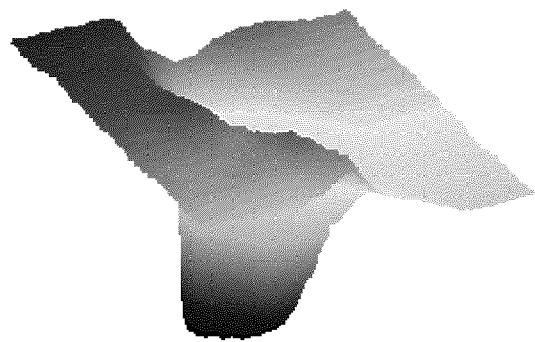
FIG. 10B shows an extracted ILM surface from a segmentation of a recovered 3D image volume with 53% missing data according to an embodiment of the invention.

The extracted ILM surface from one of the segmentations of the original 3D image is shown in FIG. 10A, where the color map represents the vertical height (to better present the 3D nature of the cup). The ILM surface extracted from the recovered volume with 53% missing data (corresponding to a sampling rate of 47%), shown in FIG. 10B, closely resembles that of the original ILM shown in FIG. 10A.

The recovered image may be deemed to have passed a test of required fidelity for potential morphometric use if the location of the ILM surface segmented from the recovered image falls within the variability of the surface segmentations performed multiple times on the original image volume by the same rater. To quantify the segmentation variability due to the manual rater, the ILM in the original 3D image was segmented thrice, each time by the same rater but without consulting the previous segmentations.

Figure 10C:
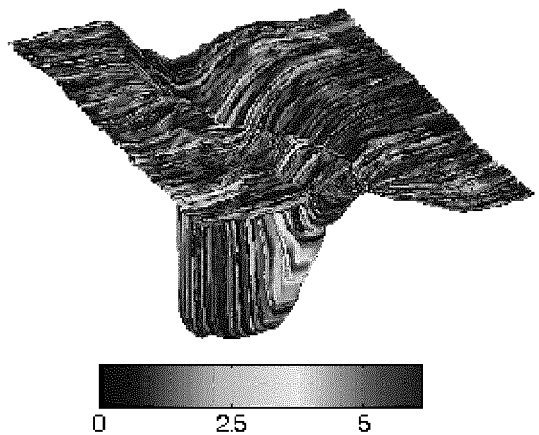
FIG. 10C shows the average ILM where the color-map represents the variance in position in the three manual segmentations of the original image volume.

Using these segmented surface images, an average ILM surface was created representing a baseline or ground truth of the ILM surface. The standard deviation of each point's position as observed in the three manual segmentations of the ILM surface was calculated, and the height or color of the colormap shown in FIG. 10C represents the variance in position in the three manual segmentations of the original image volume. The surface shown in FIG. 10C is therefore the average ILM surface where the colormap represents the variance in position in the three manual segmentations of the original image volume.

For each point on the ILM surface segmented from the reconstructed data, the relative position to the average ILM surface (the baseline) was found. This process was used to generate so-called Topographical Change Analysis (TCA) maps representing the variability in position of the ILM surface from a known baseline/ground truth. Topographical Change Analysis (TCA) maps showing the position of the ILM surface relative to the mean, overlaid on top of summed-voxels-projection images of recovered volumes at 23%, 35%, 53%, 61% and 75% missing data (corresponding to sampling rates of 77%, 65%, 47%, 39%, and 25% respectively in embodiments of the present invention) are shown in FIGS. 11A-11E, respectively. The points on the recovered ILM surface lying more than one standard deviation from the mean ILM surface are shown in FIGS. 11A-11E with red representing posterior surface location variance, and green representing anterior surface location variance in the recovered image.

Figure 11A:
FIGS. 11A-11E show topographical Change Analysis (TCA) maps showing variations in the position of an ILM surface relative to mean, overlaid on top of summed-voxels-projection images of recovered volumes at 23%, 35%, 53%, 61% and 75% missing data, respectively, according to an embodiment of the invention.
Figure 11B:
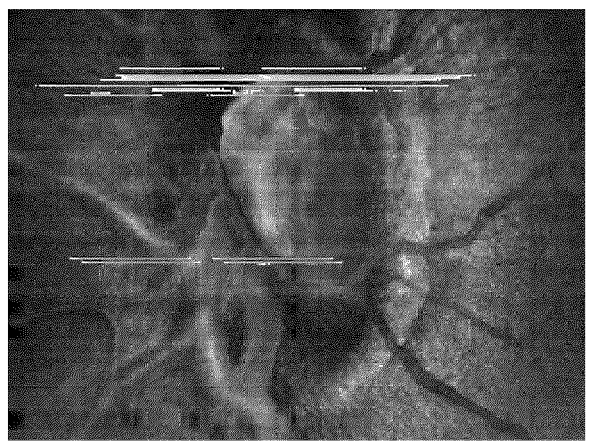
Figure 11C:
Figure 11D:
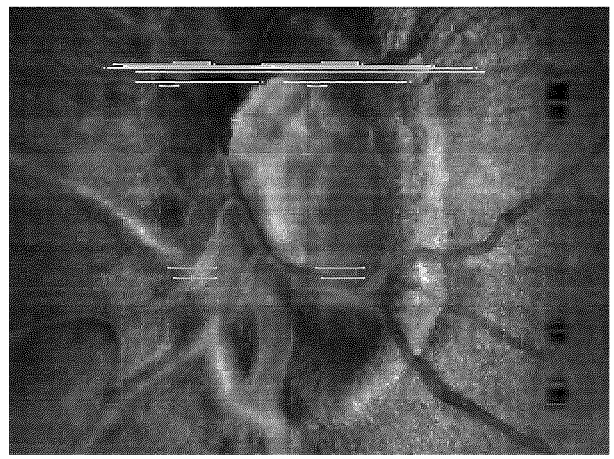
Figure 11E:
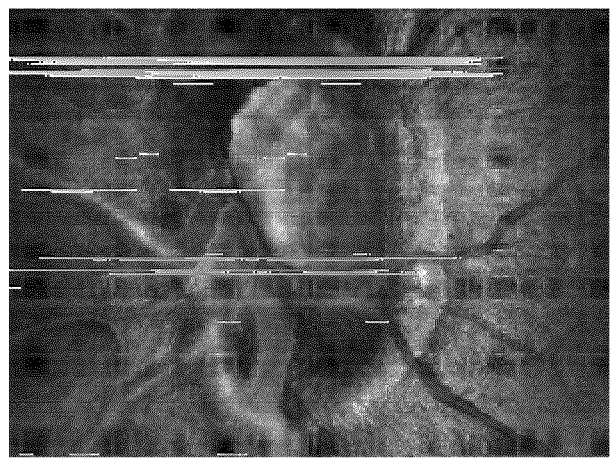

It can be seen that in the illustrative experimental embodiments discussed above, the quality of the summed-voxel-projection images begins to deteriorate at the 61% missing data volume shown in FIG. 11D (corresponding to a sampling rate of 39%), but is still acceptable even at 75% missing data shown in FIG. 11E (corresponding to a sampling rate of 25%). For the volume that was recovered from 23% missing data shown in FIG. 11A, nowhere did the segmentations fall outside the one standard deviation regions. For the other cases with more missing data as shown in FIGS. 11B-11E, most points in the image were reconstructed faithfully so that the errors in position exceeded one standard deviation in only a few locations. These were typically in slices with missing data that were located along the steeply sloping part of the ILM surface. Given that only a few locations in recovered surfaces deviated by more than one standard deviation for each of the five cases tested (as an example, <8% points on the recovered ILM surface were farther than one standard deviation in the case of 75% missing data), clinical measurements such as cup volume and area desirably did not significantly differ from the measurements made on the original volume, as shown below in Table 1.

TABLE 1

| % Missing Data | 23 | 35 | 53 | 61 | 75 |
|---|---|---|---|---|---|
| DS.A. (%) | 0.49 | 0.65 | 4.79 | 4.25 | 6.51 |
| DVOL. (%) | 0.36 | 0.81 | 1.14 | 0.85 | 0.84 |

Changes in surface area and volume of the optic nerve cup resulting from the use of images recovered from compressively sampled scans according to an embodiment of the invention were assessed to be clinically negligible.

Figure 12:
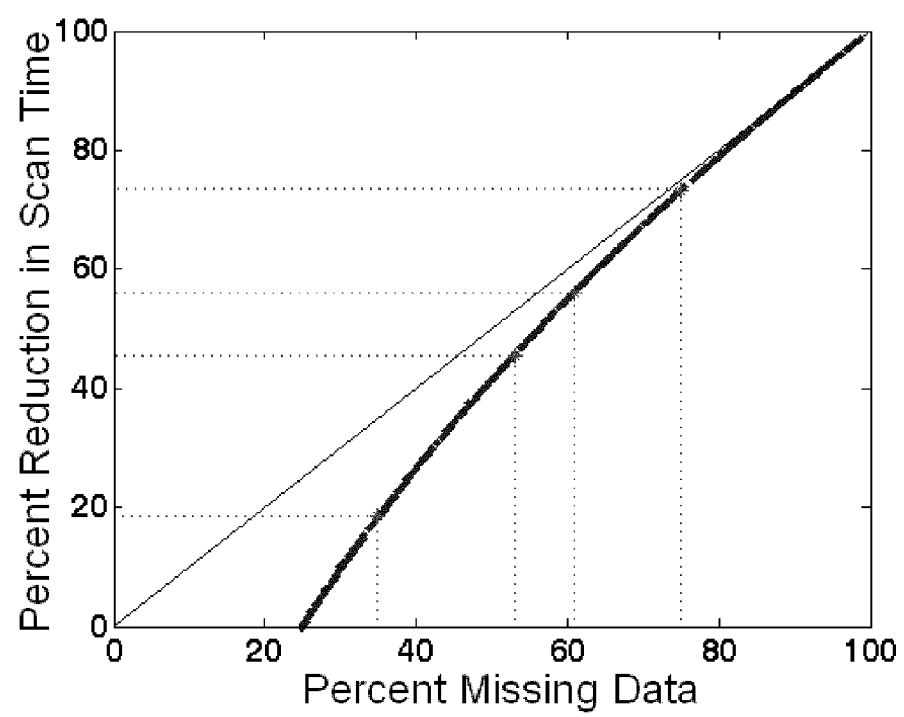
FIG. 12 illustrates a graph plotting the reduction in raster scan time as a function of percent of missing data representing the extent of OCT data under-sampling according to an embodiment of the invention.

The reduction in scan time, presented as a function of percent of missing data, is shown in FIG. 12, according to an embodiment of the invention. The benefits in reduced scan time of the proposed randomly compressed scanning patterns according to embodiments of the present invention begin to be observable when one discards approximately 25% of the data, or more (corresponding to a sampling rate of 75% or lower). Using a compressive subsampling pattern with sampling rates of 47% or 39% (corresponding to 53% or 61% missing data) roughly halved the acquisition time.

Radial OCT Imaging Using Compressive Sampling

In accordance with an alternative embodiment of the present invention, a method for rapid OCT image acquisition using radial image collection or scanning geometry and compressive sampling is provided, in which OCT acquisition of a reduced random or pseudo-random subset of radially oriented scans that make up the 3D volumetric field of view of the entire image of a subject of interest is performed during the radial scanning process. In such an alternative radial embodiment, the data comprised in the reduced random or pseudo-random subset of radial scans are further transformed and mapped to a Cartesian coordinate system with coordinates of $(r, \theta)$ on a rectangular Cartesian grid prior to compressive sampling (CS) interpolation and reconstruction, such as by using the exemplary CS interpolation and reconstruction method described above in reference to raster scanning embodiments, for example. Following such CS interpolation and reconstruction, the reconstructed radial scan data is thereafter transformed from radial coordinates of $(r, \theta)$ to an $(x, y)$ Cartesian coordinate grid to transform and restore the physically corresponding positions of the reconstructed image to a 3D Cartesian grid to facilitate storage and display of the OCT volume in a conventional 3D Cartesian grid-based system.

In one embodiment of a radial OCT image acquisition method using compressive sampling according to the present invention, the procedure comprises an OCT imaging process using sparse radial samples of the subject volume to be imaged, which in one embodiment may comprise at least a portion of the retina and/or optic nerve head of a subject, or other ophthalmological or biological subject of interest for example. In such a radial OCT sampling embodiment, the OCT data is initially acquired by randomly-spaced radial B-scans of the subject. In the context of the present invention disclosure, random-radial B-scans refer to OCT scans where the angle of a subsequent B-scan, relative to the previous B-scan, is drawn from a random or pseudo-random distribution. Suitable such radial B-scan "spokes" consisting of a fixed number of A-scans may be acquired at a random angular spacing within a range defining a maximum and minimum allowable step size, for example, to provide a randomly subsampled set of radial scans of the subject volume. In one such embodiment, the sparseness of the random radial B-scan subsampling acquisition may accordingly be determined by selecting the maximum allowable angular step size between radial B-scans.

FIG. 13(a) illustrates a schematic representation of an exemplary random radial OCT scanning pattern according to a radial embodiment of the present invention. In one such radial embodiment, a suitable random radial B-scan pattern may be constructed by selecting a first radial scan to be oriented in an arbitrary reference direction, such as horizontal or vertical, for example, and thereafter incrementing the radial angle of subsequent radial B-scans in radial angle increments that are drawn from a random or pseudo-random distribution while imposing a suitable upper limit on maximum allowable radial angle increments between any two adjacent radial B-scans, in order to define a random subsampled set of radial B-scans of the subject volume. For example, in one such embodiment, a radial angle increment between subsequent radial scans may be randomly drawn from a uniform distribution over $[0, \pi/n]$ where n may be chosen depending on the size of the smallest feature that may be desired to be resolved in the scanned image. In such a manner, selection of a radial scan geometry for OCT image acquisition may desirably allow for concentration of sampling of features in the center of the radial scanning field, while allowing for reduction of sampling concentration in areas radially distant from the center of the radial scanning field. In one such application of radial OCT imaging to the retina of a subject, the radial scanning field may be desirably centered on the optic nerve head or optic cup, such that each random radial B-scan inherently collects a denser distribution of samples close to the center of the optic nerve head, and that each radial B-scan contains a cross-section of the optic cup, regardless of the angular direction of the radial B-scan. Accordingly, random radial OCT scanning patterns may desirably provide for improved sampling density and thereby also improved resolution of desired features to be imaged near a central region of interest in the scanned subject volume, and the location of the center of the radial scan pattern may be selected to focus the increased sampling density on a particular part of a subject, such as the optic nerve head, fovea or macula in exemplary ophthalmological applications, or of other features of interest in other applications of such random radial scanning according to further embodiments of the invention.

Following random radial OCT scanning of the subject, the method comprises a step of mapping the acquired random radial B-scan or "spoke" data to place it in a Cartesian system by converting the radial (r, θ) coordinates of the radial B-scans to a Cartesian grid where θ is mapped to the x coordinate (x=θ), and r is mapped to the y coordinate (y=r) to result in a Cartesian grid in (r, θ) space, as is illustrated in a schematic view in FIG. 13(b) according to one embodiment of the present invention. Accordingly, in such an embodiment, the mapping of the (r, θ) coordinates of the radial B-scans to a Cartesian grid is substantially equivalent to "stacking" the radial B-scans vertically along the x-axis, where the placement of each radial scan "spoke" in the horizontal direction is based on the angle θ of the radial scan. Accordingly, "missing" radial scans which are not acquired due to the random subsampling of the radial B-scan pattern to be used for CS become equivalent to missing vertical lines or vertical raster scans in the Cartesian grid, as may be seen by the gaps between vertically aligned radial B-scans in the schematic view of FIG. 13(b), according to an embodiment of the invention.

Following the mapping of acquired random radial B-scans to an exemplary Cartesian grid as described above, the method comprises the step of interpolating the missing equivalent vertical raster scans in the Cartesian grid according to a suitable CS method to reconstruct a series of equivalent vertical raster scans and provide a suitably accurate interpolated set of vertically oriented B-scans in the Cartesian grid, as illustrated in schematic view in FIG. 13(c), for example. In one embodiment, the CS interpolation and reconstruction method described above for a raster scanned embodiment may be applied to interpolate and reconstruct the missing vertically oriented radial B-scans, for example. In other alternate embodiments, other potentially suitable interpolation methods may be used to interpolate and reconstruct the "missing" vertically oriented scans, such as bilinear/tri-linear or spline methods, for example.

In one embodiment, incorporating CS interpolation of the "missing" vertically oriented scans, f may be used to denote the full 3D tissue image, R to be a 3D restriction mask that restricts the image samples actually acquired, M to be a measurement basis and y to be the image samples actually acquired. In such an embodiment, the sparse image acquisition problem can now be formulated as y=RMf+n, where n is the noise in the collected data. If S is an exemplary transform domain that offers good compressibility of f, and x=Sf are the transform coefficients of f then f may desirably be exactly reconstructed by $f=S^H x$, where $S^H$ is the synthesis of S. In such an embodiment, instead of directly recovering the image f, we find a set of coefficients $\tilde{x}$ so that $\tilde{f}=S^H \tilde{x}$ is a good approximation of f. In such case, the approximating coefficients may be found by solving the following constrained optimization problem:

$$\tilde{x} = \mathrm{argmin}_x \|x\|_1 \text{ subject to } \|y - RS^H x\|_2 \leq \epsilon.$$

In one such embodiment, the above constrained optimization problem may be solved using a suitable exemplary Iterative Soft-Thresholding solver, for example.

Following the interpolation and reconstruction of the missing vertically oriented radial B-scans in the exemplary Cartesian grid as described above, the method according to one embodiment thereof comprises the step of mapping the interpolated B-scan and acquired B-scan data back onto a representative physical 3D Cartesian volume by applying the inverse of the earlier mapping, as illustrated in schematic view in FIG. 13(d). Accordingly, the reconstructed radial B-scans in (r, θ) space are mapped back to a 3D Cartesian (x,y) space using the transform θ=x and r=y to "unstack" the vertically oriented radial B-scans and return them back to radial B-scans in a 3D Cartesian grid. Accordingly, the result is that the 3D image voxels for the whole field of view of the original radial OCT scan are reconstructed in their physically corresponding positions with the missing data between the acquired radial B-scan subsampled set filled in by interpolation using CS such that the reconstructed samples are overlaid on the field of view in a 3D Cartesian grid. The use of a standard 3D Cartesian grid for defining the reconstructed OCT image desirably facilitates the storage, display, manipulation and analysis of the image using standard or conventional imaging formats and systems, for example.

Examples of Radial OCT Scanning and Compressive Sampling Method

In one exemplary embodiment, a full 3D OCT original image volume (f) was acquired by raster-scanning the optic nerve head of a healthy male subject using Fourier-domain OCT. The exemplary OCT system used for the scan had a line rate of 20 kHz, with axial and lateral resolutions of 4 μm and 25 μm, respectively. The cross sectional B-scans consisted of 512 A-scans and the full volume consisted of 400 B-scans, covering an area of approximately 3.7 mm×1.8 mm.

To simulate the sparsely sampled OCT image volume (y) that would be acquired by the above-described method of random radial B-scans to rapidly sub-sample the desired subject volume, three random radial sampling masks (R) were generated consisting of n=200, n=100 and n=60 radial B-scans, and were applied to this full OCT image f, to correspond to 61.5%, 80.9% and 88.3% missing data from the original image volume and create three sub-sampled volumes y comprising 200, 100 and 60 radial B-scans, respectively. In this exemplary embodiment, a first radial B-scan is taken oriented along the horizontal axis, and the radial direction of each subsequent radial B-scan is incremented by a random angle, randomly drawn from a normal distribution over [0, π/n], so that the maximal angular increment between adjacent radial B-scans is $\theta_{max} \leq 2\pi/n$.

FIG. 14 illustrates in its top row, a typical en-face slice image extracted from the full OCT data volume (f) showing the en-face slice represented in three frames overlaid with random radial subsampling masks (R) corresponding to 200 radial scans (61.5% missing data compared to conventional raster scan) in the left frame, 100 radial scans (80.9% missing data) in the center frame, and 60 radial scans (88.3% missing data) in the right frame, according to an embodiment of the invention. The yellow lines on the overlaid en-face slice images show locations of six exemplary extracted B-scans further shown in FIG. 14A to FIG. 14F.

Following the application of the particular radial subsampling masks (R) to the full image data volume (f), the missing radial B-scan data was interpolated and reconstructed using the CS procedure described above in the previous section, including the mapping and reverse mapping steps described above in connection with FIG. 13. In the present exemplary embodiment, an IST solver with 6 inner and 40 outer loop iterations was used to interpolate the sparse radial B-scan samples in the (r, θ) space.

FIG. 14A illustrates in a series of frames from left to right, the exemplary B-scan labeled "A" extracted from the full conventionally raster-acquired OCT volume (f) shown in the top row of FIG. 14; the same exemplary extracted B-scan corresponding to a random radial subsampling mask which discards 61.5% of the raster data (corresponding to 200 radial scans); a corresponding exemplary reconstructed B-Scan recovered from the remaining subsampled data in the 200 radial scan volume using compressive sampling; the exemplary B-scan corresponding to a random radial subsampling mask which discards 80.9% of the raster data (corresponding to 100 radial scans); a corresponding exemplary reconstructed B-Scan recovered from the remaining subsampled data in the 100 radial scan volume using compressive sampling; the exemplary B-scan corresponding to a random radial subsampling mask which discards 88.3% of the raster data (corresponding to 60 radial scans); and a corresponding exemplary reconstructed B-Scan recovered from the remaining subsampled data in the 60 radial scan volume using compressive sampling, according to an exemplary embodiment of the invention.

FIG. 14B illustrates in a series of frames from left to right, the exemplary B-scan labeled "B" extracted from the full conventionally raster-acquired OCT volume (f); the same exemplary extracted B-scan corresponding to the random radial subsampling mask comprising 200 radial scans; a corresponding exemplary reconstructed B-Scan recovered from the remaining subsampled data in the 200 radial scan volume using compressive sampling; the exemplary B-scan corresponding to a random radial subsampling mask comprising 100 radial scans; a corresponding exemplary reconstructed B-Scan recovered from the remaining subsampled data in the 100 radial scan volume using compressive sampling; the exemplary B-scan corresponding to a random radial subsampling mask comprising 60 radial scans; and a corresponding exemplary reconstructed B-Scan recovered from the remaining subsampled data in the 60 radial scan volume using compressive sampling, according to an exemplary embodiment of the invention.

FIG. 14C illustrates in a series of frames from left to right, the exemplary B-scan labeled "C" extracted from the full conventionally raster-acquired OCT volume (f) shown in the top row of FIG. 14 and the corresponding subsampled and recovered B-scan images corresponding to 200, 100 and 60 radial scan volumes, similar to as described above in FIGS. 14A and 14B, according to an exemplary embodiment of the invention.

FIG. 14D illustrates in a series of frames from left to right, the exemplary B-scan labeled "D" extracted from the full conventionally raster-acquired OCT volume (f) shown in the top row of FIG. 14 and the corresponding subsampled and recovered B-scan images corresponding to 200, 100 and 60 radial scan volumes, similar to as described above in FIGS. 14A and 14B, according to an exemplary embodiment of the invention.

FIG. 14E illustrates in a series of frames from left to right, the exemplary B-scan labeled "E" extracted from the full conventionally raster-acquired OCT volume (f) shown in the top row of FIG. 14 and the corresponding subsampled and recovered B-scan images corresponding to 200, 100 and 60 radial scan volumes, similar to as described above in FIGS. 14A and 14B, according to an exemplary embodiment of the invention.

FIG. 14F illustrates in a series of frames from left to right, the exemplary B-scan labeled "F" extracted from the full conventionally raster-acquired OCT volume shown in the top row of FIG. 14 and the corresponding subsampled and recovered B-scan images corresponding to 200, 100 and 60 radial scan volumes, similar to as described above in FIGS. 14A and 14B, according to an exemplary embodiment of the invention.

As can be seen by examining the reconstructed B-scan images and comparison to the original full volume B-scans illustrated in FIG. 14A-F according to one exemplary embodiment of the invention, it can be seen that even for subsampled volumes corresponding to only 60 acquired radial B-scans and therefore missing 88.3% of the data present in the full raster-scanned volume (f), the interpolation quality remains relatively high, and advantageously even small features in the images are still resolved.

Validation of Radial OCT Scanning and Compressive Sampling Method

Experiments were performed to quantify how the degradation in recovered images affected the measurement of anatomically meaningful parameters such as the optic nerve cup shape from ophthalmologic OCT image volumes acquired using random radial B-scans and compressive sampling recovery methods such as disclosed above according to exemplary radial scanning embodiments of the present invention. This was done by manually segmenting, using established protocols, the clinically relevant Inner Limiting Membrane ("ILM") surface for the reconstructed radial OCT scan image volumes for each of three exemplary levels of image degradation corresponding to 200, 100 and 60 radial B-scans in the exemplary original 400 raster scan full image volume. These segmentations were performed on each B-scan slice of each of the full and recovered volumes.

The Inner Limiting Membrane (ILM) of the original raster-scanned volume was independently manually segmented three times and the standard deviation of the segmentation at each point on the resulting ILM surface was computed. Subsequently, the ILM on each of the recovered surfaces was segmented by the same internal segmentation protocol and the points on each ILM surface lying more than one standard deviation away from the mean ILM surface were located. Points on each of the three degraded and recovered ILM surfaces lying more than one standard deviation from the mean ILM surface were shown in a Topographical Change Analysis (TCA) plot overlaid on top of the summed-voxels-projection images of the recovered volume.

FIG. 15A illustrates a topographical Change Analysis (TCA) map showing the position of an ILM surface relative to the mean overlaid on top of summed-voxels-projection images of a recovered OCT volume at 61.5% missing data corresponding to a 200 radial B-scan volume, according to an embodiment of the invention.

FIG. 15B illustrates a topographical Change Analysis (TCA) map showing the position of an ILM surface relative to the mean overlaid on top of summed-voxels-projection images of a recovered OCT volume at 80.9% missing data corresponding to a 100 radial B-scan volume, according to an embodiment of the invention.

FIG. 15C illustrates a topographical Change Analysis (TCA) map showing the position of an ILM surface relative to the mean overlaid on top of summed-voxels-projection images of a recovered OCT volume at 88.3% missing data corresponding to a 60 radial B-scan volume, according to an embodiment of the invention.

As can be seen by reviewing the TCA map images in FIG. 15A-C, the most predominant topographical changes occur in the regions of the recovered image where the ILM exhibits rapid vertical changes in elevation. For the recovered volume with 60 radial B-scans, less than 9% of the points in the segmented ILM surface were farther than one standard deviation from the mean ILM surface of the original full sampled volume.

The advantageous reduction in scan time required to acquire a subsampled random radial OCT B-scan volume according to the method described above according to a radial scanning embodiment of the invention, relative to the scan time required to acquire a full raster scanned volume of the same subject, is directly proportional to the number of radial B-scans acquired according to the exemplary embodiment of the invention compared to the number of original raster scans required in the raster scanned volume. The percentage reduction in scan time can be calculated by the formula $(1-n/N)$ where n is the number of acquired radial B-scans and N is the number of original raster scans. For example, the original raster scanned volume (f) described in the above-mentioned exemplary embodiment consisted of 382 raster scans, so the subsampled radial scan volume consisting of 60 radial scans corresponds to an 82.3% reduction in scan time.

In yet a further alternative embodiment of the present invention, the method described above using a random radial subsampling pattern for acquiring a reduced set of radial B-scans and use of radial to Cartesian coordinate mapping and reverse transformation in connection with CS interpolation and reconstruction of missing data may also be applied to radial imaging of other non-OCT image acquisition systems, such as ultrasound, magnetic resonance (MRI) and x-ray (including Computed Tomography) imaging systems, for example. The method of radial subsampling according to an embodiment of the invention may also be advantageously be applied to imaging of particular subject volumes where the critical or desired features to be imaged may be concentrated in one area which may be used to center a random radial scanning pattern according to the invention, so as to advantageously concentrate sampling data acquired by random radial scans of the central area and associate features, while reducing sampling of features distant from the center of the radial scan pattern, for example. In yet another embodiment, random radial scan and CS image acquisition methods according to the present invention may also advantageously be used in applications where it is desired to reduce the exposure to imaging radiation, such as in x-ray based imaging systems, for example, where the reduced number of scans and scan time offered by the present inventive methods may significantly reduce the total exposure of a subject to imaging radiation, for example. Further, the above-described random radial scanning methods using CS may also be applied to scanning subject volumes where radial symmetry or access to the subject are limited to or optimized for radial scanning over raster imaging patterns, such as in trans-rectal imaging of the prostate using ultrasound, for example, where a point source imager may be rotated through a radial scan pattern advantageously over a raster scan pattern, for example.

The exemplary embodiments herein described are not intended to be exhaustive or to limit the scope of the invention to the precise forms disclosed. They are chosen and described to explain the principles of the invention and its application and practical use to allow others skilled in the art to comprehend its teachings.

As will be apparent to those skilled in the art in light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A method for rapid Optical Coherence Tomography image acquisition comprising:
    acquiring by Optical Coherence Tomography a plurality of compressive measurements (y) representing a set of under-sampled Optical Coherence Tomography data in a Dirac domain below a Nyquist rate by sampling an object of interest at randomly spaced vertical and horizontal lines in a Cartesian geometry using a raster scan; and
    recovering a 3D volumetric Optical Coherence Tomography image (f) from the compressive measurements (y) using compressive sampling.

2. The method for rapid Optical Coherence Tomography image acquisition according to claim 1 further comprising:
    forming a sparsifying matrix (S) capable of transforming the 3D volumetric Optical Coherence Tomography image (f) into a sparse representation; and
    recovering the 3D volumetric Optical Coherence Tomography image (f) from the compressive measurements (y) based at least in part on the sparsifying matrix (S).

3. The method for rapid Optical Coherence Tomography image acquisition according to claim 2, wherein the sparsifying matrix (S) represents a matrix representation of the 3D volumetric Optical Coherence Tomography image (f) in a shift-invariant wavelet transform domain.

4. The method for rapid Optical Coherence Tomography image acquisition according to claim 2, wherein the sparsifying matrix (S) represents a matrix representation of the 3D volumetric Optical Coherence Tomography image (f) in at least one of: a curvelet transform, surfacelet transform, ridgelet transform, Gabor transform, discrete cosine transform and wavelet transform domain.

5. The method for rapid Optical Coherence Tomography image acquisition according to claim 1, wherein the compressive measurements (y) represent a range between about 25 and 77 percent of the data present in the 3D volumetric Optical Coherence Tomography image (f).

6. The method for rapid Optical Coherence Tomography image acquisition according to claim 1, wherein the compressive measurements (y) represent less than about 50 percent of the data present in the 3D volumetric Optical Coherence Tomography image (f).

7. The method for rapid Optical Coherence Tomography image acquisition according to claim 1, wherein the compressive measurements (y) represent about 25 percent of the data present in the 3D Optical Coherence Tomography image (f).

8. The method for rapid Optical Coherence Tomography image acquisition according to claim 1, wherein recovering a 3D volumetric Optical Coherence Tomography image (f) from the compressive measurements (y) using compressive sampling additionally comprises using an iterative soft thresholding solver.

9. The method for rapid Optical Coherence Tomography image acquisition according to claim 1, additionally comprising:
    analyzing said 3D volumetric Optical Coherence Tomography image (f) for at least one ophthalmological criterion.

10. A method for rapid Optical Coherence Tomography image acquisition comprising:
acquiring by Optical Coherence Tomography a plurality of compressive measurements (y) representing a set of under-sampled Optical Coherence Tomography data in a Dirac domain below a Nyquist rate by sampling an object of interest at randomly angularly spaced radial scan lines in a radial geometry using a radial scan;
mapping said compressive measurements (y) from said radial geometry to a Cartesian grid having radial coordinates;
recovering a set of recovered radial scan images (f) from the compressive measurements (y) using compressive sampling; and
mapping said recovered radial scan images from said Cartesian grid to a 3D Cartesian geometry having Cartesian coordinates to produce a physical 3D volumetric Optical Coherence Tomography image.

11. The method for rapid Optical Coherence Tomography image acquisition according to claim 10, wherein recovering a set of recovered radial scan images additionally comprises:
forming a sparsifying matrix (S) capable of transforming the recovered radial scan images (f) into a sparse representation; and
recovering the recovered set of radial scan images (f) from the compressive measurements (y) based at least in part on the sparsifying matrix (S).

12. The method for rapid Optical Coherence Tomography image acquisition according to claim 11, wherein said sparsifying matrix (S) represents a matrix representation of the set of radial scan images (f) in a shift-invariant wavelet transform domain.

13. The method for rapid Optical Coherence Tomography image acquisition according to claim 11, wherein the sparsifying matrix (S) represents a matrix representation of the set of radial scan images (f) in at least one of: a curvelet transform, surfacelet transform, ridgelet transform, Gabor transform, discrete cosine transform and wavelet transform domain.

14. The method for rapid Optical Coherence Tomography image acquisition according to claim 10, wherein recovering a set of recovered radial scan images additionally comprises using an iterative soft thresholding solver.

15. The method for rapid Optical Coherence Tomography image acquisition according to claim 10, additionally comprising:
analyzing said 3D volumetric Optical Coherence Tomography image for at least one ophthalmological criterion.

16. The method for rapid Optical Coherence Tomography image acquisition according to claim 10 wherein mapping said compressive measurements (y) from said radial geometry to a Cartesian grid having radial coordinates additionally comprises mapping a radial coordinate $\theta$ to an x Cartesian grid coordinate, and mapping a radial coordinate r to a y Cartesian grid coordinate.

17. The method for rapid Optical Coherence Tomography image acquisition according to claim 16 wherein mapping said recovered radial scan images from said Cartesian grid to a 3D Cartesian geometry having Cartesian coordinates additionally comprises using the transform $\theta=x$ and $r=y$.

18. The method for rapid Optical Coherence Tomography image acquisition according to claim 10, wherein the compressive measurements (y) represent a range between about 12 and 40 percent of the data present in the physical 3D volumetric Optical Coherence Tomography image.

19. The method for rapid Optical Coherence Tomography image acquisition according to claim 10, wherein said randomly angularly spaced radial scan lines in a radial geometry are substantially centered on said object of interest.

20. A method for rapid tomographic image acquisition comprising:
acquiring by emissive imaging means a plurality of compressive measurements (y) representing a set of under-sampled tomographic data in a Dirac domain below a Nyquist rate by sampling an object of interest at randomly angularly spaced radial scan lines in a radial geometry using a radial scan;
mapping said compressive measurements (y) from said radial geometry to a Cartesian grid having radial coordinates;
recovering a set of recovered radial scan images (f) from the compressive measurements (y) using compressive sampling; and
mapping said recovered radial scan images from said Cartesian grid to a 3D Cartesian geometry having Cartesian coordinates to produce a physical 3D volumetric tomographic image.

21. The method for rapid tomographic image acquisition according to claim 20, wherein said emissive imaging means comprises one or more of: ultrasound, magnetic resonance and x-ray imaging.

* * * * *